United States Patent
Kuang et al.

(10) Patent No.: US 10,759,845 B2
(45) Date of Patent: Sep. 1, 2020

(54) HYBRIDOMA CELL STRAIN SECRETING NIFURSOLOL RESIDUE MARKER MONOCLONAL ANTIBODY

(71) Applicant: JIANGNAN UNIVERSITY, Wuxi, Jiangsu (CN)

(72) Inventors: Hua Kuang, Jiangsu (CN); Chuanlai Xu, Jiangsu (CN); Aihong Wu, Jiangsu (CN); Liguang Xu, Jiangsu (CN); Wei Ma, Jiangsu (CN); Liqiang Liu, Jiangsu (CN); Xiaoling Wu, Jiangsu (CN); Shanshan Song, Jiangsu (CN); Yongming Hu, Jiangsu (CN)

(73) Assignee: JIANGNAN UNIVERSITY

(*) Notice: Subject to any disclaimer, the term of this patent is extended or adjusted under 35 U.S.C. 154(b) by 0 days.

(21) Appl. No.: 16/221,719

(22) Filed: Dec. 17, 2018

(65) Prior Publication Data

US 2020/0048329 A1  Feb. 13, 2020

(30) Foreign Application Priority Data

Aug. 9, 2018  (CN) .......................... 2018 1 09012498

(51) Int. Cl.
| | |
|---|---|
| C07K 16/06 | (2006.01) |
| C07K 16/12 | (2006.01) |
| C07K 16/44 | (2006.01) |
| G01N 33/12 | (2006.01) |

(52) U.S. Cl.
CPC ........ *C07K 16/065* (2013.01); *C07K 16/1289* (2013.01); *C07K 16/44* (2013.01); *G01N 33/12* (2013.01)

(58) Field of Classification Search
None
See application file for complete search history.

(56) References Cited

FOREIGN PATENT DOCUMENTS

| CN | 106124653 A | | 11/2016 |
|---|---|---|---|
| CN | 108330102 A | * | 7/2018 |
| WO | 2007024735 A2 | | 3/2007 |
| WO | 2008115580 A2 | | 9/2008 |

OTHER PUBLICATIONS

Zhang YB, Qiao Ho, Chen C, et al. Determination of nitrofurans metabolites residues in aquatic products by ultra-performance liquid chromatography—tandem mass spectrometry [J]. Food Chem, 2016, 192: 612-617.
Vahl M. Analysis of nifursol residues in turkey and chicken meat using liquid chromatography—tandem mass spectrometry [J]. Food Addit Contam, 2005, 22(2): 120-127.
Kaufmann A, Butcher P, Maden K, et al. Determination of nitrofuran and chloramphenicol residues by high mass spectrometry versus tandem quardrupole mass spectrometry [J]. Anal Chim Acta, 2015, 862: 41-52.
Chen Y, Guo L, Liu L, et al. An ultrasensitive immunochromatographic strip for fast screening of twenty-seven sulfonamides in honey and pork liver samples based on a monoclonal antibody[J]. Journal of Agricultural and Food Chemistry, 2017:acs.jafc.7b03190.
Wang Z, Zou S, Xing C, et al. Preparation of a monoclonal antibody against testosterone and its use in development of an immunochromatographic assay[J]. Food and Agricultural Immunology, 2016, 27(4):12.

* cited by examiner

*Primary Examiner* — Brian Gangle
(74) *Attorney, Agent, or Firm* — Enshan Hong; VLP Law Group LLP

(57) ABSTRACT

A hybridoma cell strain secreting a nifursol residue marker monoclonal antibody with CGMCC No. 18525 is prepared in the following way: BALB/c mice are subjected to the first immunization with a complete Freund's adjuvant, subjected to booster immunization with an incomplete Freund's adjuvant for four times, and subjected to rush immunization once with nifursol residue marker complete antigen without a Freund's adjuvant so that the BALB/c mice are immunized; the spleen cells of the immunized mice with high titer and low IC50 were fused with mouse myeloma cells by a PEG method, and the fused cells are screened through indirect competitive ELISA and subcloned three times. The monoclonal antibody secreted by this cell strain has good specificity and detection sensitivity (IC50 value of 2 μg/L) to the nifursol residue marker and can be used for residue detection of the nifursol residual marker in food.

2 Claims, 1 Drawing Sheet

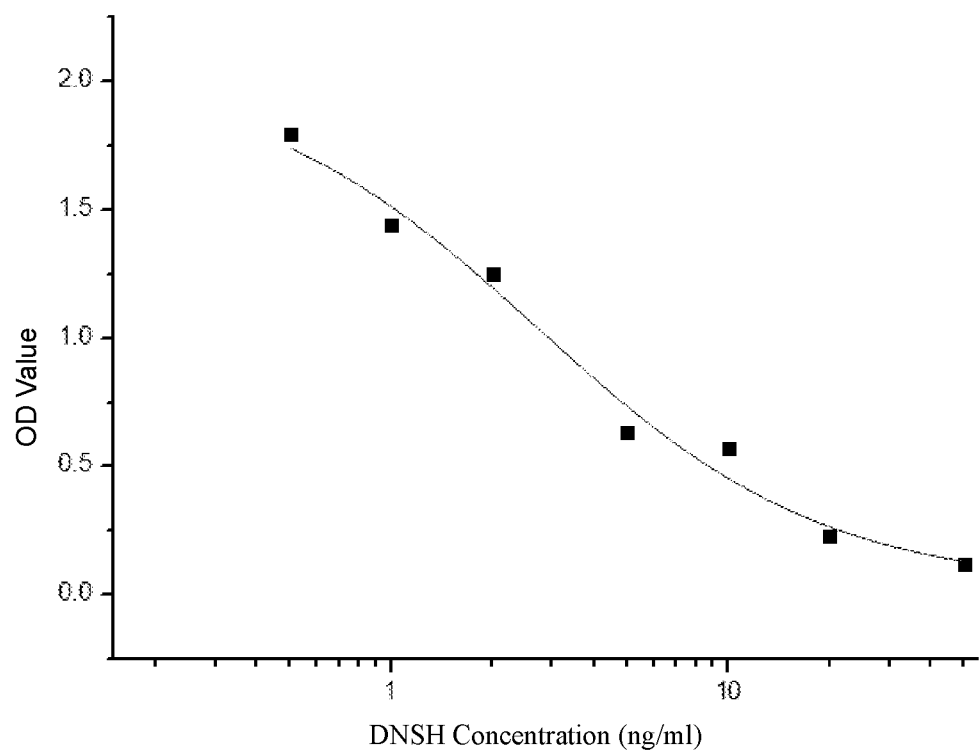

HYBRIDOMA CELL STRAIN SECRETING NIFURSOLOL RESIDUE MARKER MONOCLONAL ANTIBODY

CROSS-REFERENCES TO RELATED APPLICATIONS

This application claims priority from China Patent Application Serial Number 2018109012498, which was filed on Aug. 9, 2018, the entire content of which is incorporated herein as reference.

BACKGROUND OF THE INVENTION

1. Technical Field

The invention relates to a hybridoma cell strain secreting a nifursol residue marker monoclonal antibody and belongs to the field of food safety immunoassay.

2. Background Art

Nifursol is a nitrofuran antibacterial agent, which is often used as a feed additive in foreign countries to prevent and treat protozoal infections of livestock. During use, nifursol technical is rapidly metabolized in animals into the metabolites 3,5-Dinitrosalicylic acid hydrazide (DNSH) and 5-nitro-2-furoic acid, both of which can be considered as nifursol residue markers. These metabolites bind tightly to proteins in animals to form stable bound residues, which are present in the animals for a long time and have certain toxicity. Therefore, it is of great significance and market value to establish a rapid and effective method for detecting residue markers of meloxicam nifursol.

Nifursol remains in the form of metabolites in animals, with low levels of residues and complex matrices. At present, high-sensitivity and high-selectivity techniques are used for the determination of such low residual levels of veterinary drug residues, mainly by GC (Gas Chromatography), HPLC (High Performance Liquid Chromatography), LC-MS (Liquid Chromatography-Mass Spectrometry), LC-MS/MS (Liquid Chromatography-Mass Spectrometry/Mass Spectrometry), and other instrumental methods; however, these methods have the disadvantages of cumbersome operation, time consuming, and relatively expensive cost, and cannot achieve rapid detection of a large number of samples. Therefore, it is of great significance to establish a rapid and simple method for detecting residue markers of meloxicam nifursol.

Enzyme-linked immunosorbent assay (ELISA) is an extremely efficient, sensitive and rapid method for detecting samples, and with low purity requirement and easy operation, ELISA is suitable for rapid on-site detection of a large number of samples. However, the premise of use of enzyme-linked immunosorbent assay for detecting meloxicam is to obtain a monoclonal antibody with high specificity and sensitivity to meloxicam. Therefore, it is very critical to find a method for preparing a monoclonal antibody with high specificity and high sensitivity to a nifursol residue marker.

The inventors attempted to prepare monoclonal antibodies for nifursol residue markers by hybridoma cells; however, in the preparation of a hybridoma cell strain capable of secreting a nifursol residue marker monoclonal antibody, how to prepare a nifursol residue marker hapten and a nifursol residue marker complete antigen and how to cause mice to generate strong immunity require further research; how to enable the prepared hybridoma cell strain to successfully secrete the nifursol residue marker monoclonal antibody also requires further research; how to enable the secreted nifursol residue marker monoclonal antibody to have high specificity and sensitivity requires further research too.

SUMMARY OF THE INVENTION

The object of the invention is to obtain a hybridoma cell strain capable of secreting a nifursol residue marker monoclonal antibody. With good specificity and detection sensitivity ($IC_{50}$ value of 2 µg/mL) to a nifursol residue marker, the nifursol residue marker monoclonal antibody secreted by this hybridoma cell strain can be used to establish an immunological assay method for the nifursol residue marker to detect the residue of the nifursol residue marker in food.

The technical solution of the invention is as follows:

The invention provides a hybridoma cell strain secreting a nifursol residue marker monoclonal antibody. The hybridoma cell strain has been preserved at the China General Microbiological Culture Collection Center (Address: No. 3, #1 Yard, Beichen West Road, Chaoyang District, Beijing) on Oct. 14, 2019 with CGMCC No. 18525.

The invention provides a preparation method of the hybridoma cell strain secreting a nifursol residue marker monoclonal antibody, comprising the following steps:

Step 1: preparing a nifursol residue marker (DNSH) hapten, synthesizing a DNSH complete antigen through the DNSH hapten, mixing the DNSH complete antigen with an equal amount of oil, and then adding an emulsifier for emulsifying to obtain an incomplete Freund's adjuvant, and adding mycobacteria to the incomplete Freund's adjuvant to obtain a complete Freund's adjuvant, wherein the oil is a paraffin oil or a vegetable oil, the emulsifier is lanolin or Tween 80, and the mycobacteria comprise dead BCG;

Step 2: subcutaneously injecting the prepared Freund's adjuvant into BALB/c mice in back for multiple immunizations, wherein the complete Freund's adjuvant is used in first immunization and the incomplete Freund's adjuvant is used in booster immunization;

Step 3: collecting blood from the mice subjected to the above immunization process, detecting the serum immunopotency and immunosuppressive ability of the mice by indirect ELISA, and screening out the immunized mice with a high DNSH antibody content in serum.

Step 4: performing the final booster immunization on the screened mice with the incomplete Freund's adjuvant, and then performing rush immunization by intraperitoneal injection, wherein the rush immunization is carried out using the DNSH complete antigen without a Freund's adjuvant; and Step 5: fusing spleen cells of the BALB/c mice subjected to the rush immunization with myeloma cells; culturing the fused cells through a medium, detecting positive cell wells by ic-ELISA, and further determining the inhibitory effect of the positive cell wells by ic-ELISA; subcloning the positive cell wells with the best inhibitory effect by a limiting dilution method; and finally screening to obtain the hybridoma cell strain capable of secreting a nifursol residue marker monoclonal antibody;

wherein the molecular formula of the DNSH hapten in Step 1 is as follows:

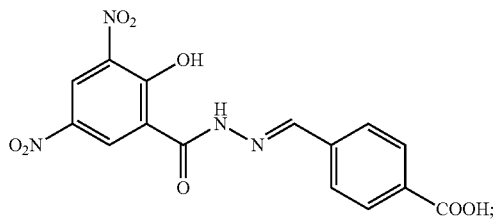 [SMILES: O=C(O)c1ccc(/C=N/NC(=O)c2cc([N+](=O)[O-])cc([N+](=O)[O-])c2O)cc1]

the molecular formula of the DNSH complete antigen in Step 1 is as follows:

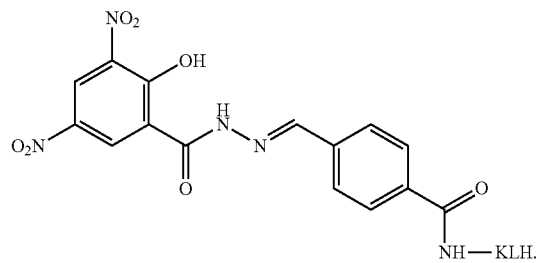

In one embodiment of the invention, the interval between the first immunization and the booster immunization in Step 2 and Step 4 is 28 days, the interval between boosting immunizations is 21 days, and the interval between the booster immunization and the rush immunization is 21 days.

In one embodiment of the invention, the immunization process in Step 2 and Step 4 includes one first immunization, four booster immunizations, and one rush immunization.

In one embodiment of the invention, the blood collection in Step 3 is performed on the 7th day after the end of the third immunization process.

In one embodiment of the invention, the cell fusion in Step 5 is performed on the 3rd day after the end of the rush immunization.

In one embodiment of the invention, the cell fusion in Step 5 is carried out by a polyethylene glycol (PEG 1500) method.

In one embodiment of the invention, the medium in Step 5 is RPMI-1640 medium.

In one embodiment of the invention, subcloning is carried out three times in Step 5.

The invention provides application of the hybridoma cell strain secreting a nifursol residue marker monoclonal antibody or the preparation method of the hybridoma cell strain secreting the nifursol residue marker monoclonal antibody in the aspect of preparation of the nifursol residue marker monoclonal antibody.

The invention provides a nifursol residue marker hapten with a molecular formula as follows:

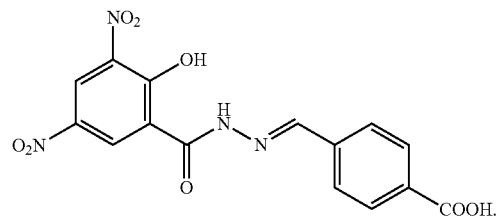

The invention provides a preparation method of the nifursol residue marker hapten, comprising: dissolving p-carboxybenzaldehyde in water, and adding HCl solution to obtain a mixed solution 1; adding DMF and a nifursol residue marker (DNSH) to the mixed solution, stirring and refluxing to obtain a mixed solution 2; centrifuging, washing and drying the obtained mixed solution 2 to obtain a crude product; and separating the crude product to obtain a DNSH hapten with a molecular formula as follows:

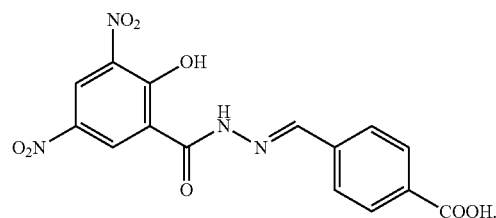 [SMILES: O=C(O)c1ccc(/C=N/NC(=O)c2cc([N+](=O)[O-])cc([N+](=O)[O-])c2O)cc1]

In one embodiment of the invention, the method comprises: dissolving 0.5 g of p-carboxybenzaldehyde in 10 ml of water, adding 3 ml of HCl solution to obtain a mixed solution 1; and adding DMF and 1.02 g of DNSH to the mixed solution while magnetically stirring, magnetically stirring at 60° C., refluxing overnight to obtain a mixed solution 2; centrifuging, washing and drying the obtained mixed solution 2 to obtain a crude product; and carrying out column chromatography separation on the crude product to obtain the DNSH hapten.

In one embodiment of the invention, the concentration of the HCl solution is 1 mol/L.

The invention provides application of the nifursol residue marker hapten or the preparation method of the nifursol residue marker hapten in the aspect of preparation of a nifursol residue marker complete antigen, a hybridoma cell strain secreting a nifursol residue marker monoclonal antibody, and a nifursol residue marker monoclonal antibody.

The invention provides a nifursol residue marker complete antigen, and the molecular formula of the nifursol residue marker complete antigen is as follows:

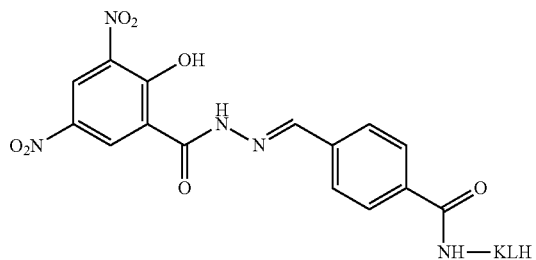

The invention provides a preparation method of the nifursol residue marker complete antigen, comprising: dissolving a nifursol residue marker hapten, EDC (1-(3-dimethylaminopropyl)-3-ethylcarbodiimide hydrochloride) and NHS (N-hydroxysuccinimide) in DMF (N,N-dimethylformamide), and stirring for activation to obtain a solution A; dissolving KLH in a carbonate buffer solution (CB solution) to obtain a solution B; and adding the solution A to the solution B, and stirring for reaction to obtain a nifursol residue marker complete antigen.

The nifursol residue marker hapten has a molecular formula as follows:

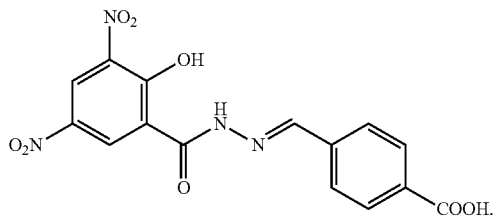 [SMILES: O=C(O)c1ccc(/C=N/NC(=O)c2cc([N+](=O)[O-])cc([N+](=O)[O-])c2O)cc1]

In one embodiment of the invention, the method comprises: dissolving 4.5 mg of a nifursol residue marker hapten, 2.0 mg of EDC (1-(3-dimethylaminopropyl)-3-ethylcarbodiimide hydrochloride) and 1.0 mg of NHS (N-hydroxysuccinimide) in DMF (N,N-dimethylformamide), and stirring for activation at room temperature for 4 h to obtain a solution A; dissolving 5 mg of KLH in 2 mL of a CB solution to obtain a solution B; and dropwise adding the solution A to the solution B, and stirring at room temperature for reaction overnight to obtain a nifursol residue marker complete antigen.

In one embodiment of the invention, the CB solution has a concentration of 0.05 mol/L and a pH of 9.6.

The invention provides application of the nifursol residue marker complete antigen or the preparation method of the nifursol residue marker complete antigen in the aspect of preparation of a hybridoma cell strain secreting a nifursol residue marker monoclonal antibody, and a nifursol residue marker monoclonal antibody.

The invention provides a nifursol residue marker coating antigen with a molecular formula as follows:

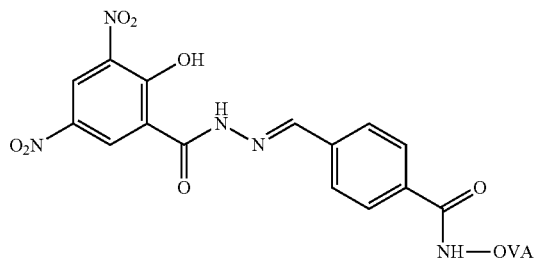

The invention provides a preparation method of the nifursol residue marker coating antigen, comprising: dissolving a nifursol residue marker hapten, EDC (1-(3-dimethylaminopropyl)-3-ethylcarbodiimide hydrochloride) and NHS (N-hydroxysuccinimide) in DMF (N,N-dimethylformamide), and stirring for activation to obtain a solution A; dissolving OVA in a CB solution to obtain a solution B; and adding the solution A to the solution B, and stirring for reaction to obtain a nifursol residue marker coating antigen.

The nifursol residue marker hapten has a molecular formula as follows:

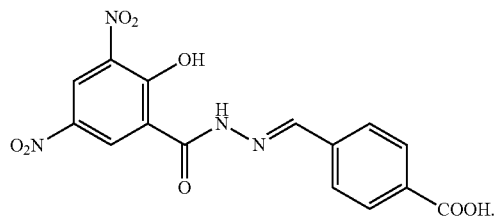

In one embodiment of the invention, the method comprises: dissolving 5 mg of a nifursol residue marker hapten, 2.0 mg of EDC (1-(3-dimethylaminopropyl)-3-ethylcarbodiimide hydrochloride) and 1.0 mg of NHS (N-hydroxysuccinimide) in DMF (N,N-dimethylformamide), and stirring at room temperature for activation for 4 h to obtain a solution A; dissolving OVA in 2 ml of a CB solution to obtain a solution B; and dropwise adding the solution A to the solution B, and stirring at room temperature for reaction overnight to obtain a nifursol residue marker coating antigen.

The invention provides application of the nifursol residue marker coating antigen or the preparation method of the nifursol residue marker coating antigen in the aspect of preparation of a hybridoma cell strain secreting a nifursol residue marker monoclonal antibody, and a nifursol residue marker monoclonal antibody.

The invention provides a nifursol residue marker monoclonal antibody which is secreted by a hybridoma cell strain with CGMCC No. 18525.

The invention provides a preparation method of the nifursol residue marker monoclonal antibody, comprising: getting BALB/c mice ready, intraperitoneally injecting paraffin oil, and then intraperitoneally injecting a hybridoma cell strain with CGMCC No. 18525, collecting ascites after the injection, purifying the ascites, and storing the obtained monoclonal antibody at a low temperature.

In one embodiment of the invention, the method comprises: getting 8-10 weeks old BALB/c mice ready, intraperitoneally injecting 1 mL of paraffin oil in each mouse, and 7 days later, intraperitoneally injecting a $1 \times 10^6$ hybridoma cell strain with CGMCC No. 18525 in each mouse, collecting ascites from the 7th day, purifying the ascites by an octanoic acid-ammonium sulfate method, and storing the obtained monoclonal antibody at −20° C.

The invention provides application of the nifursol residue marker monoclonal antibody in the aspect of identification of the nifursol residue marker.

The invention provides a test kit prepared from the hybridoma cell strain secreting a nifursol residue marker monoclonal antibody or the nifursol residue marker hapten, or the nifursol residue marker complete antigen, or the nifursol residue marker monoclonal antibody.

Beneficial Effect (1) The nifursol residue marker monoclonal antibody prepared according to the invention has good specificity and detection sensitivity ($IC_{50}$ value of 2 μg/mL) to a nifursol residue marker.

(2) The invention provides a concept of synthesis of a brand-new nifursol residue marker complete antigen and coating antigen.

(3) The cell strain secreting a nifursol residue marker monoclonal antibody, prepared according to the invention, can be used for immunoassay detection.

Preservation of Biological Materials

A hybridoma cell strain secreting a nifursol residue marker monoclonal antibody, classified as: a monoclonal cell strain, preserved at the China General Microbiological Culture Collection Center (Address: No. 3, #1 Yard, Beichen West Road, Chaoyang District, Beijing) on Oct. 14, 2019 with CGMCC No. 18525.

BRIEF DESCRIPTION OF THE DRAWINGS

In the drawings:
FIG. 1 is a standard curve of inhibition of the nifursol residue marker monoclonal antibody of the invention against the nifursol residue marker.

DESCRIPTION OF PREFERRED EMBODIMENTS

Media involved in the following embodiments are as follows:

RPMI-1640 medium (mg/L): L-arginine 290, L-asparagine 50, L-aspartate 20, L-cystine dihydrochloride 65.15, L-glutamic acid 20, glycine 10, L-histidine 15, L-hydroxyproline 20, L-isoleucine 50, L-leucine 50, L-lysine hydrochloride 40, L-methionine 15. L-phenylalanine 15, L-proline 20, L-serine 30, L-threonine 20, L-tryptophan 5, L-tyrosine 23.19, L-valine 20, p-aminobenzoic acid 1, calcium nitrate 100, anhydrous magnesium sulfate 48.84, anhydrous sodium dihydrogen phosphate 676.13, potassium chloride 400, sodium chloride 6000, glucose 2000, reduced glutathione 1, phenol red 5, L-glutamine 300, biotin 0.2, D-calcium pantothenate 0.25, folic acid 1, i-inositol 35, nicotinamide 1, choline chloride 3, pyridoxine hydrochloride 1, riboflavin 0.2, thiamine hydrochloride 1, vitamin B12 0.005, sodium bicarbonate 2000.

Reagents involved in the following embodiments are as follows:

Carbonate buffer solution (CBS): 1.59 g of $Na_2CO_3$ and 2.93 g of $NaHCO_3$ are weighed and separated dissolved in a small amount of double distilled water; the two solutions are mixed; double distilled water is added to the mixed solution till about 800 mL and the mixed solution is mixed to be uniform; the pH is adjusted to 9.6, and double distilled water is added till the mixed solution reaches 1000 mL and the obtained solution is stored at 4° C. for later use.

Phosphate buffer solution (PBS): 8.00 g of NaCl, 0.2 g of KCl, 0.2 g of $KH_2PO_4$, 2.9 g of $Na_2HPO_4.12 H_2O$ are dissolved in 800 mL of pure water, the pH is adjusted to 7.2-7.4 with NaOH or HCl, and the solution is maintained at a constant volume of 1000 mL.

Wash solution (PBST): 0.5 mL of Tween-20 is added to 1000 mL of a 0.01 mol/L PBS solution (pH 7.4).

PBST: PBS containing 0.05% Tween 20.

Antibody dilution: a wash buffer solution containing 0.1% gelatin.

TMB developing solution: Solution A: 18.43 g of $Na_2HPO_4.12H_2O$ and 9.33 g of citric acid are added with pure water to 100 mL; B solution: 60 mg of TMB is dissolved in 1000 mL of ethylene glycol. The solution A and the solution B are mixed at a ratio of 1:5 to obtain TMB (a developing solution, mixed when necessary).

Detection methods involved in the following embodiments are as follows:

Method for detecting the inhibition rate of a nifursol residue marker standard: DNSH standard solutions with concentrations of 0 µg/L, 0.5 µg/L, 1 µg/L, 2 µg/L, 5 µg/L, 10 µg/L, 20 µg/L and 40 µg/L are prepared respectively with the PBS; the standard solutions are added to a closed ELISA plate, 50 µL per well, 2 wells per solution, 50 µL of an anti-DNSH monoclonal antibody diluted at a ratio of 1:32000 is then added to each well and reacts at 37° C. for 0.5 h, and then the plate is washed and patted dry; 100 µL of an HRP-labeled goat anti-mouse IgG secondary antibody diluted with the PBS containing 0.1% gelatin at a ratio of 1:3000 is added to each well, and reacts at 37° C. for 0.5 h, and then the plate is washed and patted dry; 100 µL of the TMB developing solution is added to each well; after development at 37° C. for 15 min, 50 µL of 2M $H_2SO_4$ stop solution is added to each well, and the absorbance (OD) is measured at 450 nm; an inhibition standard curve is drawn using Origin plotting software (results shown in FIG. 1).

Example 1

Synthesis of a Nifursol Residue Marker Hapten 0.5 g of p-carboxybenzaldehyde is dissolved in 10 ml of water, 3 ml of HCl solution with a concentration of 1 mol/L is added to obtain a mixed solution 1; and DMF and 1.02 g of a nifursol residue marker (DNSH) are added to the mixed solution while magnetically stirring, and then the mixed solution is stirred magnetically at 60° C. and refluxed overnight to obtain a mixed solution 2; the obtained mixed solution 2 is centrifuged, washed and dried to obtain a crude product; and column chromatography separation is carried out on the crude product to obtain the nifursol residue marker hapten.

Example 2

Synthesis of a Nifursol Residue Marker Complete Antigen 4.5 mg of a nifursol residue marker hapten, 2.0 mg of EDC (1-(3-dimethylaminopropyl)-3-ethylcarbodiimide hydrochloride) and 1.0 mg of NHS (N-hydroxysuccinimide) are dissolved in DMF (N,N-dimethylformamide), and stirred for activation at room temperature for 4 h to obtain a solution A; 5 mg of KLH is dissolved in 2 mL of the CB solution with a concentration of 0.05 mol/L and a pH of 9.6 to obtain a solution B; and the solution A is dropwise added to the solution B, and stirred at room temperature for reaction overnight to obtain a nifursol residue marker complete antigen.

Example 3

Synthesis of a Nifursol Residue Marker Coating Antigen 5 mg of thiamethoxam hapten (TMX-COOH) and 4.8 mg of N-hydroxysuccinimide (NETS) are dissolved in 300 µL of anhydrous N,N-dimethylformamide (DMF), and the solution is stirred at room temperature to react for 10 min to obtain a TMX-COOH solution; 7.6 mg of 1-(3-dimethylaminopropyl)-3-ethylcarbodiimide hydrochloride (EDC) is dissolved in 100 µL of anhydrous DMF and then added to the TMX-COOH solution, and stirred at room temperature to react for 6-8 h to obtain a solution A; 10 mg of chicken OVA is diluted with 1 mL of a phosphate buffer solution (PBS) with a concentration of 0.01 mmol/L and a pH of 7.4 to obtain a solution B; the solution A is slowly added dropwise to the solution B to react to obtain a reaction solution; the reaction solution is dialyzed with the PBS solution to remove the unreacted small molecular hapten to obtain a coating antigen (TMX-COOH-OVA).

Example 4

Preparation of a Hybridoma Cell Strain Secreting a Nifursol Residue Marker Monoclonal Antibody 1. Acquisition of Immunity in Animals Healthy 6-8 week old BALB/c mice are selected for immunization. After a DNSH complete antigen (1 mg/mL) is emulsified uniformly with an equal amount of a Freund's adjuvant, BALB/c mice are immunized with the emulsified DNSH complete antigen by subcutaneous injection at a dose of 100 μL for each mouse. The first immunization is performed with a complete Freund's adjuvant, the booster immunization is performed with an incomplete Freund's adjuvant, and the immunization dose for the rush immunization is half of the dose for previous immunization; the Freund's adjuvants are directly used through intraperitoneal injection after being mixed with normal saline; the immunization interval of the immunizations is three weeks. After the third immunization, blood samples are taken at intervals of one week to detect serum titer and inhibitory effect; the mice with the best inhibitory effect are selected and are subject to rush immunization 21 days after the fifth immunization.

2. Cell Fusion

Three days after the rush immunization, cell fusion is carried out according to the conventional PEG (polyethylene glycol, with a molecular weight of 4000) method. The specific steps are as follows:

(1) The mouse spleens are aseptically taken, ground and screened through a 200 mesh cell sieve to obtain a spleen cell suspension, and cells are counted;

(2) SP2/0 cells are collected, suspended in a RPMI-1640 basal medium, and subjected to cell counting;

(3) Spleen cells and SP2/0 cells are mixed at a ratio of 1:10, centrifuged and fused with 50% PEG for 1 min, then the RPMI-1640 basal medium is added from slow to fast, the solution is centrifuged and then suspended in an RPMI-1640 screening medium containing 20% fetal bovine serum and 2% 50×HAT, and then added to a 96-well cell culture plate and cultured in an incubator at 37° C. in a 5% $CO_2$ atmosphere.

3. Cell Screening and Cell Strain Establishment

The medium of the fused cells is semi-changed with an RPMI-1640 screening medium on the third day of cell fusion, and then completely changed with an RPMI-1640 transition medium containing 20% fetal bovine serum and 1% 100×HT on the 5th day. The cell supernatant is taken for screening on the 7th day.

The screening is divided into two steps: the first step is to select positive cell wells by ic-ELISA, the second step is to use a nifursol residue marker as a standard and measure the inhibitory effect of the positive cells by ic-ELISA.

Cell wells with a good inhibitory effect to the nifursol residual marker standard are selected and subcloned by a limiting dilution method. The same method is used for detection and repeated three times to obtain a cell strain.

Embodiment 5: Preparation and Identification of a Nifursol Residue Marker Monoclonal Antibody 8-10 weeks old BALB/c mice are taken and each intraperitoneally injected with 1 mL of sterile paraffin oil, and 7 days later, intraperitoneally injected with a 1×10⁶ hybridoma cell strain; ascites is collected from the 7th day and purified by an octanoic acid-ammonium sulfate method.

Under an acidic condition, n-octanoic acid can precipitate heterologous proteins other than IgG immunoglobulin in ascites, then centrifugation is performed to remove the precipitate; the IgG monoclonal antibody is then precipitated with an ammonium sulfate solution with the equivalent saturability, centrifuged to remove the supernatant, dissolved in 0.01 M PBS solution (with a pH of 7.4), and dialyzed for desalting to finally obtain the purified monoclonal antibody, and the purified monoclonal antibody is stored at −20° C.

By using an indirect competitive ELISA, the $IC_{50}$ of the monoclonal antibody is determined to be 2 μg/L, indicating a good sensitivity to DNSH. Thus the monoclonal antibody can be used for nifursol residue immunoassay.

Embodiment 6: Application of the Nifursol Residue Marker Monoclonal Antibody The monoclonal antibody prepared from the hybridoma cell strain via in-vivo ascites is applied to the ELISA addition recovery test of DNSH, and the specific steps are as follows:

(1) the coating antigen with a coating concentration of 0.3 μg/mL diluted with the CBS is used to coat a 96-well ELISA plate, 100 μL per well, at 37° C. for 2 h; the plate is then washed with the PBST wash solution three times, 200 μL per well, 3 min each time, and patted dry;

(2) the plate is closed with the CBS containing 0.2% gelatin, 200 μL per well, at 37° C. for 2 h; the plate is washed with the PBST wash solution three times, 200 μL per well, 3 min each time, and patted dry;

(3) the DNSH standard solutions with concentrations of 0 μg/L, 0.5 μg/L, 1 μg/L, 2 μg/L, 5 μg/L, 10 μg/L, 20 μg/L and 40 μg/L are prepared respectively with the PBS; the standard solutions and to-be-tested samples are respectively added to the closed ELISA plate, 50 μL per well, 3 wells for each sample; 50 μL of an anti-DNSH monoclonal antibody diluted at a ratio of 1:32000 is then added to each well and reacts at 37° C. for 0.5 h, and then the plate is washed and patted dry;

(4) 100 μL of an HRP-labeled goat anti-mouse IgG secondary antibody diluted with the PBS containing 0.1% gelatin at a ratio of 1:3000 is added to each well, and reacts at 37° C. for 0.5 h, and then the plate is washed and patted dry;

(5) 100 μL of the TMB developing solution is added to each well; after development at 37° C. for 15 min, 50 μL of 2M $H_2SO_4$ stop solution is added to each well, and the absorbance (OD) is measured at 450 nm;

(6) Addition recovery and sample preparation:

three parts of 2±0.02 g homogenized chicken are weighed and placed in a 50 ml centrifuge tube respectively, and then added with 15 ml of a mixed solution of methanol and water (1:1), shaken for 10 min, and centrifuged at 4000 r/min for 5 min to remove liquid; the residue is added with 10 ml of 0.2 mol/L hydrochloric acid, homogenized at 10000 r/min for 1 min, and then added with 5 ppb, 10 ppb, 100 ppb DNSH respectively, mixed uniformly by vortexing for 30 s, and then shaken for 30 min. 2 ml of 0.3 mol/L potassium phosphate is added and the pH is adjusted to 7.4 with 0.2 mol/L NaOH, 10 ml of ethyl acetate is added, and the mixture is shaken for extraction for 10 min, centrifuged at 10,000 r/min for 10 min, and the ethyl acetate layer is collected. The ethyl acetate layer is dried at 40° C. with N2, dissolved in 1 ml of a 0.1% aqueous solution of formic acid, and then defatted with 3 ml of acetonitrile saturated n-hexane, and the aqueous phase at the bottom is used as an ELISA sample extract.

The addition recovery test is carried out by indirect competitive ELISA, and the recovery rates are 85%, 86%, and 90%, respectively.

Although the invention has been disclosed in the above preferred embodiments, the invention is not limited thereto, and any person skilled in the art can make various changes and modifications without departing from the spirit and scope of the invention. The scope of the invention should be defined by the claims.

What is claimed is:

1. A hybridoma cell strain secreting a nifursol residue marker monoclonal antibody, preserved at the China General Microbiological Culture Collection Center (Address: No. 3, #1 Yard, Beichen West Road, Chaoyang District, Beijing) on Oct. 14, 2019 with CGMCC No. 18525.

2. A nifursol residue marker monoclonal antibody which is secreted by the hybridoma cell strain of claim 1.

* * * * *